(12) United States Patent
Jain et al.

(10) Patent No.: US 10,537,253 B2
(45) Date of Patent: Jan. 21, 2020

(54) DETECTING LIVE TISSUES USING SIGNAL ANALYSIS

(71) Applicant: Samsung Electronics Company, Ltd., Suwon, Gyeong gi-Do (KR)

(72) Inventors: Jawahar Jain, Los Altos, CA (US); Cody Wortham, Mountain View, CA (US); James Young, Menlo Park, CA (US); Sajid Sadi, San Jose, CA (US); Pranav Mistry, Campbell, CA (US)

(73) Assignee: Samsung Electronics Company, Ltd., Suwon (KR)

( * ) Notice: Subject to any disclaimer, the term of this patent is extended or adjusted under 35 U.S.C. 154(b) by 300 days.

(21) Appl. No.: 15/298,003

(22) Filed: Oct. 19, 2016

(65) Prior Publication Data

US 2017/0249429 A1    Aug. 31, 2017

Related U.S. Application Data

(60) Provisional application No. 62/300,033, filed on Feb. 25, 2016.

(51) Int. Cl.
*G01N 33/48* (2006.01)
*A61B 5/021* (2006.01)
*A61B 5/00* (2006.01)
*A61B 5/024* (2006.01)
*G06G 7/58* (2006.01)

(52) U.S. Cl.
CPC ........ *A61B 5/02116* (2013.01); *A61B 5/0022* (2013.01); *A61B 5/02416* (2013.01)

(58) Field of Classification Search
None
See application file for complete search history.

(56) References Cited

U.S. PATENT DOCUMENTS

| | | | |
|---|---|---|---|
| 9,241,635 | B2 | 1/2016 | Yuen |
| 9,282,902 | B2 | 3/2016 | Richards |
| 2002/0137995 | A1 | 9/2002 | Heckel |
| 2004/0204865 | A1 | 10/2004 | Lee |
| 2006/0094943 | A1 | 5/2006 | Van Slyke |
| 2009/0227853 | A1 | 9/2009 | Wijesiriwardana |
| 2013/0066173 | A1 | 3/2013 | Addison |
| 2014/0257049 | A1 | 9/2014 | Soundarapandian |
| 2014/0275852 | A1 | 9/2014 | Hong |
| 2015/0245782 | A1 | 9/2015 | Morland |
| 2015/0265217 | A1 | 9/2015 | Penders |
| 2015/0359436 | A1 | 12/2015 | Shim |
| 2016/0022201 | A1 | 1/2016 | Arnold |
| 2016/0022220 | A1 | 1/2016 | Lee |
| 2016/0029968 | A1 | 2/2016 | Lerner |
| 2016/0058367 | A1 | 3/2016 | Raghuram |

FOREIGN PATENT DOCUMENTS

| | | |
|---|---|---|
| EP | 0690694 A1 | 1/1996 |
| WO | WO 2013/036718 A1 | 3/2013 |
| WO | WO 2015/084376 | 6/2015 |

OTHER PUBLICATIONS

ISR and WO for International Application No. PCT/KR2017/002038, dated May 30, 2017.
Extended European Search Report for Application No. 17756849.0-1132, dated Nov. 26, 2018.

*Primary Examiner* — Eric S Dejong
(74) *Attorney, Agent, or Firm* — Baker Botts L.L.P.

(57) ABSTRACT

In one embodiment, a method includes accessing first time-series data based on electromagnetic radiation in a first spectrum and second time-series data based on electromagnetic radiation in a second spectrum. The method also includes comparing the first time-series data with the second time-series data and determining, based on the comparison, (1) whether a stopping condition associated with a device has occurred or (2) whether a discarding condition associated with the first time-series data or the second time-series data has occurred.

27 Claims, 10 Drawing Sheets

DETECTING LIVE TISSUES USING SIGNAL ANALYSIS

PRIORITY

This application claims the benefit, under 35 U.S.C. § 119(e), of U.S. Provisional Patent Application No. 62/300,033 titled "Detecting Live Tissues Using PPG Analysis" and filed 25 Feb. 2016, which is incorporated herein by reference.

TECHNICAL FIELD

This disclosure generally relates to analyzing data gathered by a device by detecting electromagnetic radiation.

BACKGROUND

Mobile electronic devices provide a user with access to computing capabilities even as the user moves about various locations. Examples of mobile electronic devices include mobile phones, media players, laptops, tablets, personal digital assistants (PDAs), or hybrid devices that include functionality of multiple devices of this type.

Mobile electronic devices may be part of a communication network such as a local area network, wide area network, cellular network, the Internet, or any other suitable network. A mobile electronic device may use a communication network to communicate with other electronic devices, for example, to access remotely-stored data, access remote processing power, access remote displays, provide locally-stored data, provide local processing power, or provide access to local displays. For example, networks may provide communication paths and links to servers, which may host applications, content, and services that may be accessed or utilized by users via mobile electronic devices. The content may include text, video data, audio data, user settings or other types of data. Networks may use any suitable communication protocol or technology to facilitate communication between mobile electronic devices, such as, for example, BLUETOOTH, IEEE WI-FI (802.11a/b/g/n/ac), or Transmission Control Protocol/Internet Protocol (TCP/IP).

DESCRIPTION OF EXAMPLE EMBODIMENTS

Figure 1:
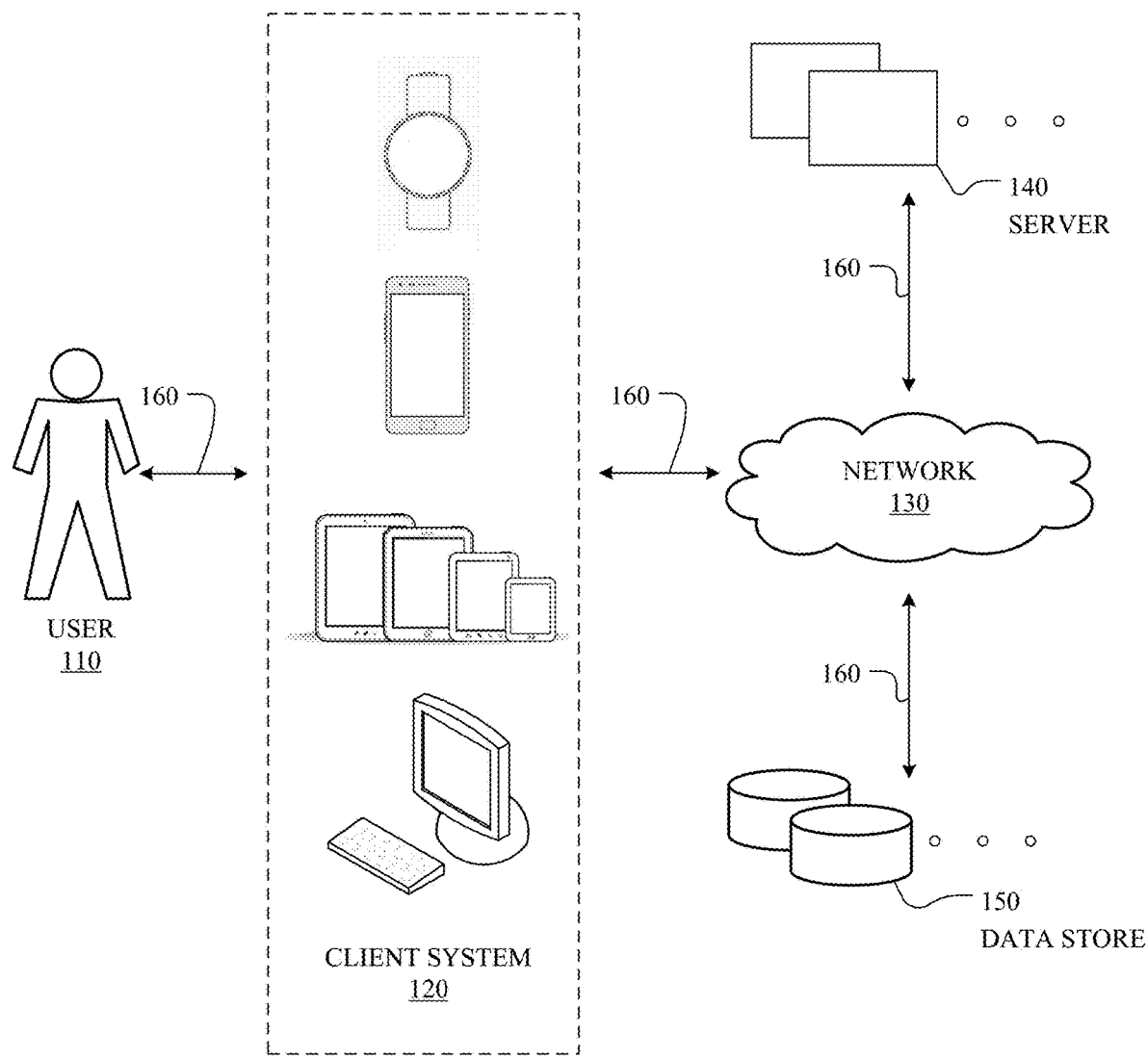
FIG. 1 illustrates an example network environment for particular embodiments of an optical detection system for internal body tissues and bone.

FIG. 1 illustrates an example network environment 100 for particular embodiments of a system for detecting biological tissue. Network environment 100 includes a user 110, a client system 120, a network 130, one or more servers 140, and one or more data stores 150. User 110, client system 120, servers 140, and data stores 150 may be connected to each other by network 130 via links 160. Although FIG. 1 illustrates a particular arrangement of user 110, client system 120, network 130, servers 140, and data stores 150, this disclosure contemplates any suitable arrangement of user 110, client system 120, network 130, servers 140, and data stores 150. As an example and not by way of limitation, two or more of client system 120, servers 140, and data stores 150 may be connected to each other directly, bypassing network 130. As another example, two or more of client system 120, servers 140, and data stores 150 may be physically or logically co-located with each other in whole or in part. Moreover, although FIG. 1 illustrates a particular number of user 110, client system 120, network 130, servers 140, and data stores 150, this disclosure contemplates any suitable number of user 110, client system 120, network 130, servers 140, and data stores 150. As an example and not by way of limitation, network environment 100 may include multiple users 110, client systems 120, networks 130, servers 140, and data stores 150.

In particular embodiments, user 110 may be an individual (e.g., human user) who interacts or communicates with client system 120. In particular embodiments, client system 120 may be any suitable computing device, such as, for example, a wearable computing device, a mobile computing device, a smartphone, a cellular telephone, a tablet computer, a laptop computer, a personal computer, an augmented/virtual reality device, or any combination thereof. User 110 may interact with one or more of these devices. In addition, these devices may communicate with each other via network 130, directly (e.g., by non-network connections), by any other suitable methods, or any combination thereof. As an example and not by way of limitation, the devices of client system 120 may communicate with network 130 via a wireless communications protocol, such as Wi-Fi or BLUETOOTH. In particular embodiments, client system 120 may include a web browser, such as MICROSOFT INTERNET EXPLORER, GOOGLE CHROME or MOZILLA FIREFOX, and may have one or more add-ons, plug-ins, or other extensions, such as TOOLBAR or YAHOO TOOLBAR. A user at client system 120 may enter a Uniform Resource Locator (URL) or other address directing the web browser to a particular server (such as server 140), and the web browser may generate a Hyper Text Transfer Protocol (HTTP) request and communicate the HTTP request to server. The server may accept the HTTP request and communicate to client system 120 one or more Hyper Text Markup Language (HTML) files responsive to the HTTP request. Client system 120 may render a webpage based on the HTML files from the server for presentation to the user. This disclosure contemplates any suitable webpage files. As an example and not by way of limitation, webpages may render from HTML files, Extensible Hyper Text Markup Language (XHTML) files, or Extensible Markup Language (XML) files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a webpage encompasses one or more corresponding webpage files (which a browser may use to render the webpage) and vice versa, where appropriate.

In particular embodiments, network 130 may be any suitable network. As an example and not by way of limitation, one or more portions of network 130 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 130 may include one or more networks.

In particular embodiments, links 160 may connect client system 120, servers 140, and data stores 150 to network 130 or to each other. This disclosure contemplates any suitable links 160. In particular embodiments, one or more links 160 include one or more wireline (such as for example Digital Subscriber Line (DSL) or Data Over Cable Service Interface Specification (DOCSIS)), wireless (such as for example Wi-Fi or Worldwide Interoperability for Microwave Access (WiMAX)), or optical (such as for example Synchronous Optical Network (SONET) or Synchronous Digital Hierarchy (SDH)) links. In particular embodiments, one or more links 160 each include an ad hoc network, an intranet, an extranet, a VPN, a LAN, a WLAN, a WAN, a WWAN, a MAN, a portion of the Internet, a portion of the PSTN, a cellular technology-based network, a satellite communications technology-based network, another link 160, or a combination of two or more such links 160. Links 160 need not necessarily be the same throughout network environment 100. One or more first links 160 may differ in one or more respects from one or more second links 160.

In particular embodiments, servers 140 may be any suitable servers. Each server 140 may be a unitary server or a distributed server spanning multiple computers or multiple datacenters. Servers 140 may be of various types, such as, for example and without limitation, web server, file server, application server, exchange server, database server, proxy server, another server suitable for performing functions or processes described herein, or any combination thereof. In particular embodiments, each server 140 may include hardware, software, or embedded logic components or a combination of two or more such components for carrying out the appropriate functionalities implemented or supported by server 140.

In particular embodiments, data stores 150 may be any suitable data stores. Data stores 150 may be used to store various types of information. In particular embodiments, the information stored in data stores 150 may be organized according to specific data structures. In particular embodiments, each data store 150 may be a relational, columnar, correlation, or other suitable database. Data store 150 may include networked storage such as cloud storage or other network accessible storage. Additionally or alternatively, data store 150 may include local storage within or directly attached to any of the devices of client system 120, such as solid state drives ("SSDs") or hard disk drives ("HDDs"). Although this disclosure describes or illustrates particular types of components and uses of these component of network environment 100, this disclosure contemplates any suitable types of components, any suitable network topology (e.g., including a standalone-device topology), and any suitable uses for these components of network environment 100.

Figure 2A:
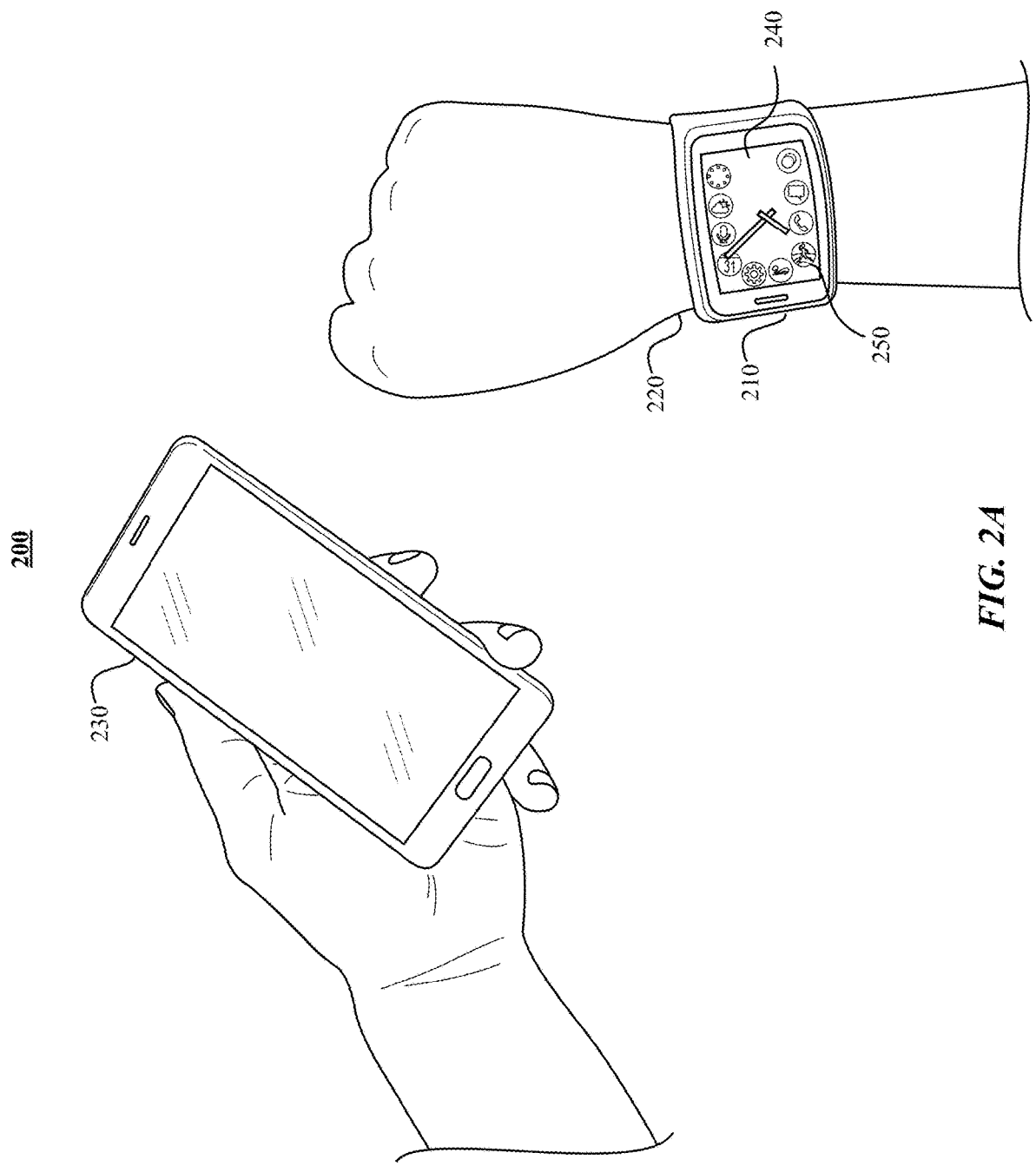
FIGS. 2A-2B illustrate example health monitoring systems including systems and devices according to particular embodiments.
Figure 2B:
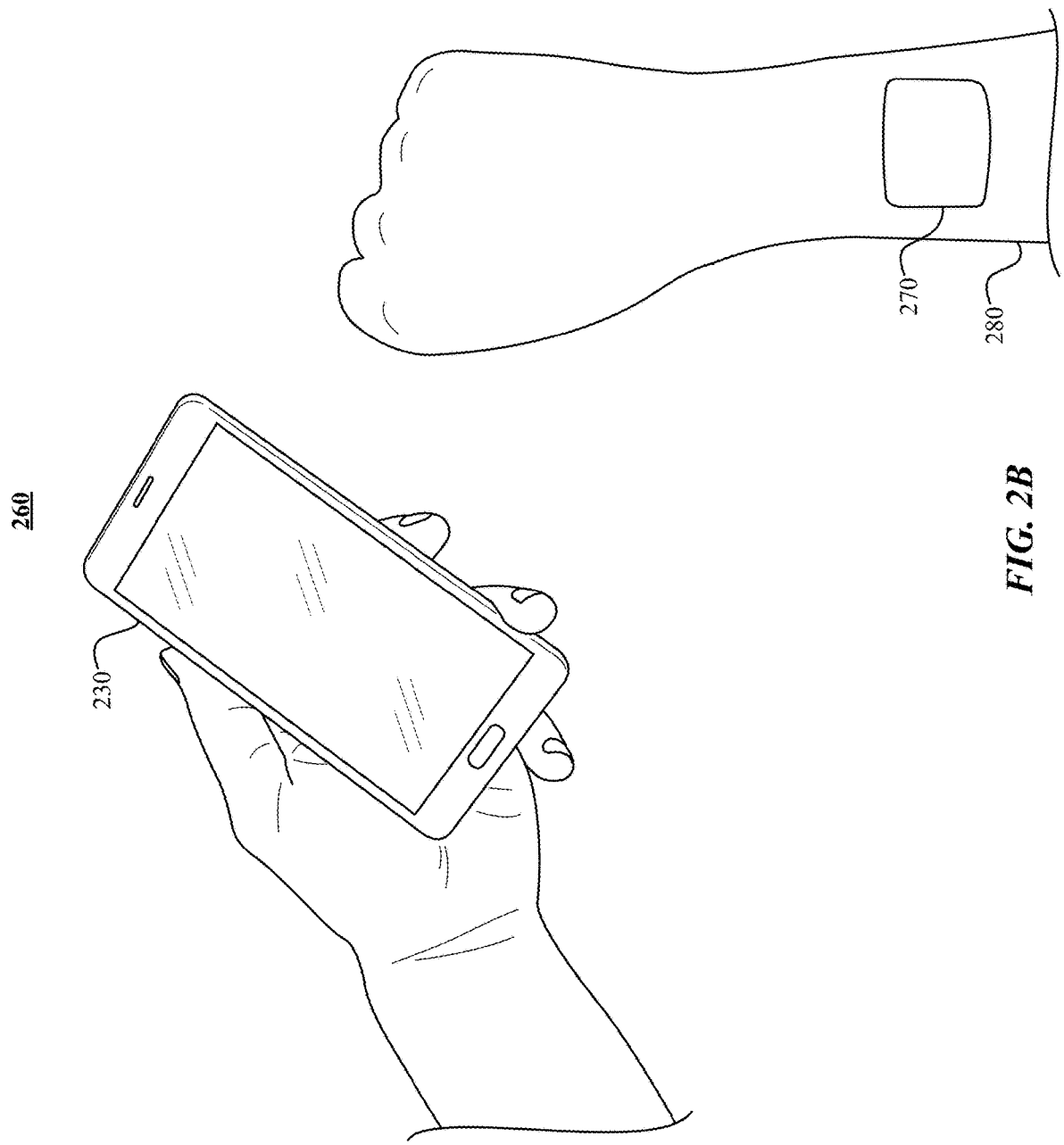

FIG. 2A illustrates an example health monitoring system 200 including systems and devices according to particular embodiments, and FIG. 2B illustrates another example health monitoring system 270 including systems and devices according to particular embodiments. In particular embodiments, as shown in FIG. 2A, health monitoring system 200 may include a health monitoring device 210 (e.g., positioned on user wrist 220) and a mobile electronic device 230. Health monitoring device 210 may be a wearable electronic device (e.g., a device of client system 120) that can be worn on a portion of the user's body, such as an arm, wrist, finger, leg, ankle, toe, torso, neck, head, any other suitable portion of the body, or any combination thereof. Health monitoring device 210 may include a user interface 240, which may include a watch-like user interface in addition to one or more applications 250 (e.g., a weather application, an exercise application, a chat application, etc.). In particular embodiments, as shown in FIG. 2B, health monitoring system may include a health monitoring patch 270 (e.g., positioned on user arm 280) and mobile electronic device 230. Similar to health monitoring device 210, health monitoring patch 270 may be adhered to a portion of the user's body, such as an arm, wrist, leg, ankle, torso, neck, head, any other suitable portion of the body, or any combination thereof.

In particular embodiments, health monitoring device 210 and/or health monitoring patch 270 may connect to mobile electronic device 230 directly or via network 130, which may facilitate interaction between and/or transfer of data between health monitoring device 210 and mobile electronic device 230 and/or health monitoring patch 270. In particular embodiments, mobile electronic device 230 may be a smartphone-like device. Health monitoring device 210, health monitoring patch 270, and mobile electronic device 230 may be connected to network 130, servers 140, data stores 150, or any combination thereof. Data (e.g., heart rate, stress level, sleep time, emotional state, etc.) may be stored on health monitoring device 210, health monitoring patch 270, mobile electronic device 230, other client systems 120, data stores 150, other suitable databases, or any combination thereof. In addition, the processing of the data and computations of particular algorithms (as discussed below) may be performed by health monitoring device 210, health monitoring patch 270, mobile electronic device 230, on servers 140, by any other client system 120, other suitable devices/systems, or any combination thereof. In particular embodiments, the processing of the data and computations of particular algorithms may be performed by accessing user data, frame of reference/baseline data, medical data, other relevant data, or any combination thereof, from data stores 150 via network 130. Although this disclosure describes a health monitoring system in a particular manner, this disclosure contemplates a health monitoring system in any suitable manner and with any suitable components.

Figure 3:
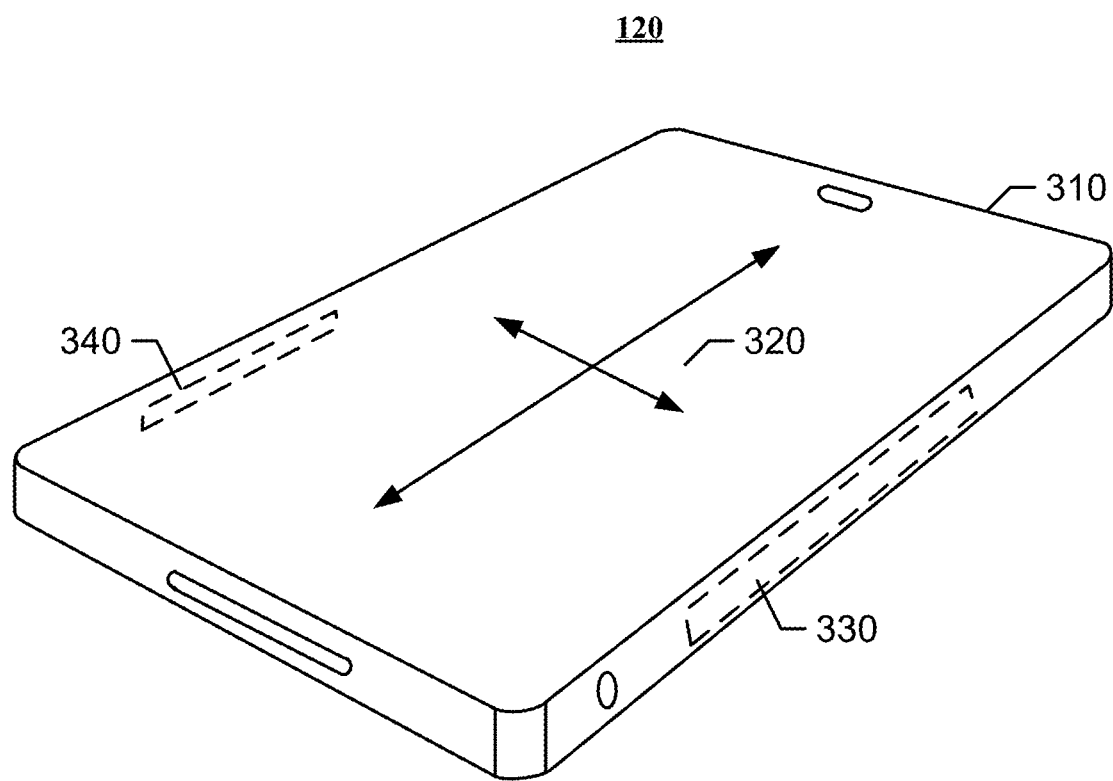
FIG. 3 illustrates an example mobile client.

FIG. 3 illustrates an example mobile client system 120 (e.g., mobile electronic device 230). This disclosure contemplates mobile client system 120 taking any suitable physical form. In particular embodiments, mobile client system 120 may be a computing system as described below. As an example and not by way of limitation, mobile client system 120 may be a single-board computer system (SBC) (such as, for example, a computer-on-module (COM) or system-on-module (SOM)), a laptop or notebook computer system, a mobile telephone, a smartphone, a personal digital assistant (PDA), a tablet computer system, or a combination of two or more of these. In particular embodiments, mobile client system 120 may have a display screen 310 and a touch sensor 320 as an input component. In the example of FIG. 3, touch sensor 320 is incorporated on a front surface (e.g., display screen 310) of mobile client system 130. Touch sensor 320 may detect the presence and location of a touch (e.g., from a finger of a user) or the proximity of an object (e.g., a stylus). In the case of capacitive touch sensors, there may be two types of electrodes: transmitting and receiving. These electrodes may be connected to a controller designed to drive the transmitting electrodes with electrical pulses and measure the changes in capacitance from the receiving electrodes caused by a touch or proximity input. In particular embodiments, a user may be presented with a user interface ("UI") of one or more applications (e.g., mobile applications) on screen display 310 of mobile client system 120, and the user may interact with the UI of each of the applications via touch sensor 320.

In the example of FIG. 3, one or more antennae 330, 340 may be incorporated into one or more sides of mobile client system 120. Antennae 330, 340 are components that convert electric current into radio waves, and vice versa. During transmission of signals, a transmitter applies an oscillating radio frequency (RF) electric current to terminals of antenna 330, 340, and antenna 330, 340 radiates the energy of the applied the current as electromagnetic (EM) waves. During reception of signals, antennae 330, 340 convert the power of an incoming EM wave into a voltage at the terminals of antennae 330, 340. The voltage may be transmitted to a receiver for amplification.

In particular embodiments, mobile client system 120 many include a communication component coupled to antennae 330, 340 for communicating with an Ethernet or other wire-based network or a wireless NIC (WNIC), wireless adapter for communicating with a wireless network, such as for example a WI-FI network or modem for communicating with a cellular network, such third generation mobile telecommunications (3G), or Long Term Evolution (LTE) network. This disclosure contemplates any suitable network and any suitable communication component for it. As an example and not by way of limitation, mobile client system 120 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As another example, mobile client system 300 may communicate with a wireless PAN (WPAN) (such as, for example, a BLUETOOTH WPAN), a WI-FI network, a WI-MAX network, a cellular telephone network (such as, for example, a Global System for Mobile Communications (GSM), 3G, or LTE network), or other suitable wireless network or a combination of two or more of these. Mobile client system 120 may include any suitable communication component for any of these networks, where appropriate.

In particular embodiments, the communication component coupled to antennae 330, 340 of mobile client system 120 may be configured to determine location data based on global positioning system (GPS) signals, cellular triangulation, wireless hotspots, or any suitable methods for determining location data. In particular embodiments, the location service of mobile client system 120 may use one or more methods of location determination, such as for example, using the location of one or more cellular towers, crowd-sourced location information associated with a WI-FI hotspot, or a GPS function of mobile client system 120. As an example and not by way of limitation, the application may use GPS data as the primary source of location information depending at least in part on whether mobile client system 120 is able to acquire GPS data within a pre-determined period of time. As another example, if mobile client system 120 is unable to acquire the GPS data within the pre-determined sampling duration, the application may use the location determined using one or more cellular towers or WI-FI hotspots. Although this disclosure describes a location service using particular methods of location determination, this disclosure contemplates a location service using any suitable method or combination of methods of location detection.

In particular embodiments, a device may analyze one or more sets of data gathered by one or more sensors to determine whether a stopping condition or a discarding condition for the sensors has occurred. The stopping condition or discarding condition for the sensors may correspond to a situation in which the sensors are not sensing an object which the sensor are configured to sense or a situation in which the data gathered by the sensors are compromised by noise or is otherwise determined to be unreliable. Detection of the stopping condition or discarding condition may trigger, for example, turning off one or more of the sensors or discarding data gathered by the sensors within a particular time period. Particular embodiments may improve the power consumption performance or measurement accuracy of the device or one or more other devices associated with the sensors.

Long-term continuous monitoring can facilitate determining the health status of a patient, and can be used to assess user health in critical situation such as when the user is recuperating from a heart failure. Such monitoring of a patient's health status may be carried out using smart watches (e.g., Samsung Gear S2) or other wearable devices. The wearable devices may be power limited, especially when operated at the full sampling rate. Full sampling rate operation may be needed for determining bio-markers accurately to assist the patient being monitored, e.g., users in serious health conditions. Not only are wearable devices power hungry but they may also need daily charging to ensure that there is no data loss. This may lead to the notion of using two devices interchangeably for monitoring the health status of the patient; one during the day and another during the night. Particular bio-sensors may continue collecting data even when their corresponding devices are not on the patient's body or are improperly fitted to the patient's body. This may lead to erroneous data being collected and can present significant challenges to the analysis of such data. This may negatively impact the accuracy of treatment decisions made by the patient or related medical professionals.

The problem described above may similarly occur for smart phones and other mobile devices that may be used to monitor a user's health status. For example, if a smart phone is disengaged from a user's finger (e.g., due to an unavoidable interruption which must be attended to) and placed on a table, one or more bio-sensors integrated on the smart phone may continue gathering data as if the phone is still in proximity with the finger. The smart phone may also continue computing the bio-markers for the user using the erroneous data gathered from the table. This may cause continued consumption of the smart phone's power, erroneously computed bio-markers, or interruption of data collection that may require continuity (e.g., collection of data for measuring stress).

Particular embodiments may address the aforementioned problems and determine whether one or more bio-sensors are sensing live tissues by analyzing data collected by the bio-sensors. The analysis may comprise one or more stages, each corresponding to one or more data-analysis tools. The data-analysis tools may comprise, for example, calculation of the variance or co-variance of data collected by one or more bio-sensors, comparing a pulsatile amplitude with a non-pulsatile value of data collected by one or more bio-sensors, calculating a mutual information ("MI") value between data collected by one or more bio-sensors and their delayed images, another suitable data-analysis tool, or any combination thereof. A device analyzing the data may aggregate the results of one or more of the stages and determine whether one or more stopping or discarding conditions have occurred. It may then power off itself, turn off one or more bio-sensors, or discard data for a particular time range based on the determined stopping or discarding conditions.

Figures 4A, 4B, 4C:
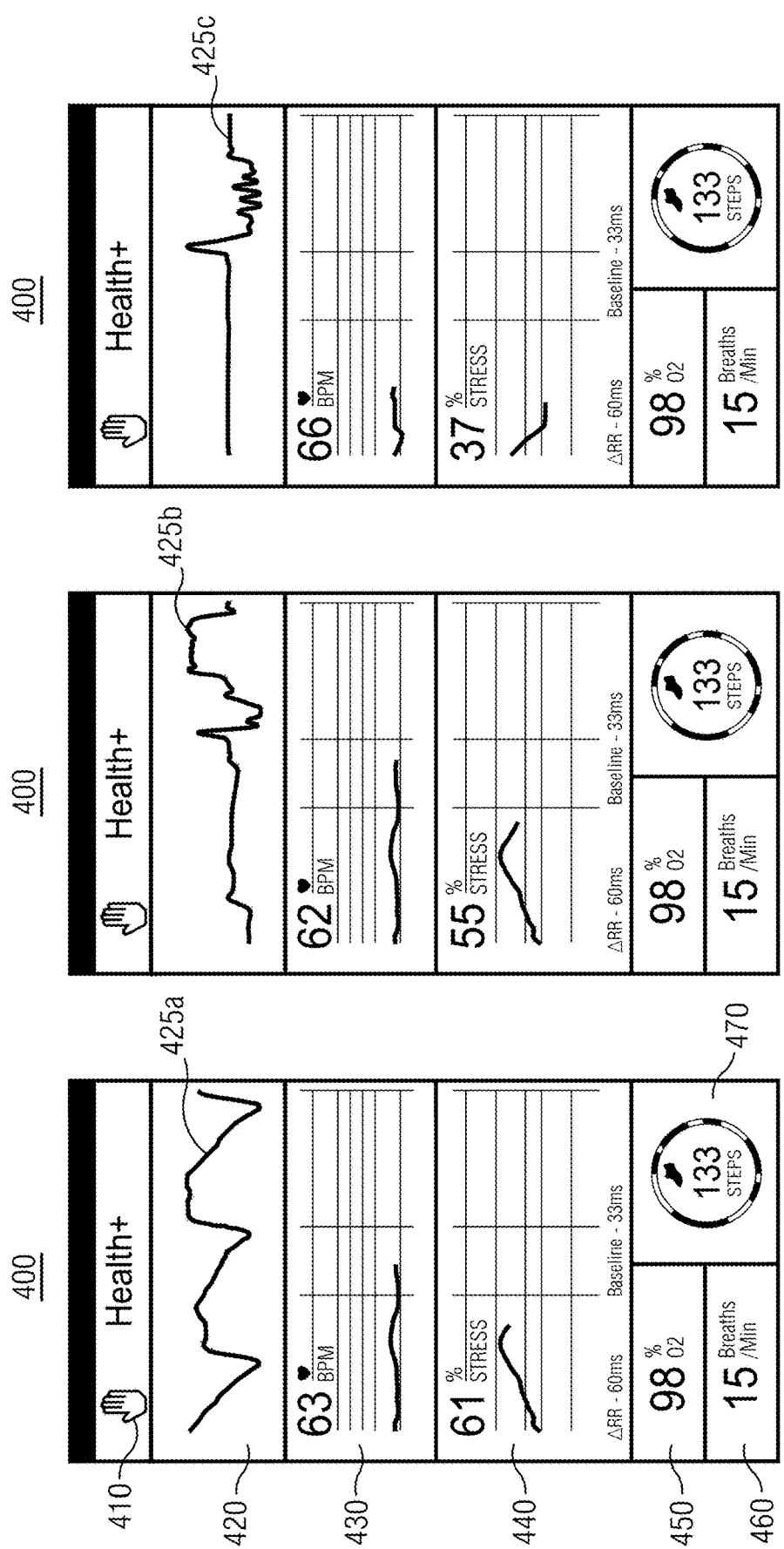
FIGS. 4A-4C illustrate example user interfaces displaying example signals detected by a health monitoring device according to particular embodiments.

FIGS. 4A-4C illustrate example user interfaces displaying example signals detected by a health monitoring device according to particular embodiments. Particular embodiments may be deployed as or implemented on a device comprising a non-transitory computer-readable memory and one or more processors. In particular embodiments, the device may be a health monitoring device 210. The health monitoring device 210 may be a wearable device, which may comprise a mobile phone, a smart watch, a fitness tracker, a wristband, a necklace, a head-worn device, a piece of clothing, a ring, a chest drape, another suitable wearable device, or any combination thereof. The health monitoring device 210 may comprise one or more sensors. In particular embodiments, the device may comprise one or more bio-sensors configured to detect one or more signals from live tissues and gather data from such signals. In particular embodiments, the bio-sensors may comprise any suitable sensor for measuring a periodical biological signal, such as a signal corresponding to a person's heartbeat (e.g., electrocardiography "ECG" data). In particular embodiments, one or more of the bio-sensors may detect electromagnetic radiation in one or more different spectrums and generate time-series data based on the detected electromagnetic radiation. The detection process of a particular bio-sensor may comprise illuminating a live tissue with electromagnetic radiation in a particular spectrum and detecting electromagnetic radiation passing through or backscattered from the live tissue. As an example and not by way of limitation, one or more of the bio-sensors may be photoplethysmographic ("PPG") sensors. A PPG sensor may illuminate a patient's skin using a pulse oximeter and measure changes in light absorption using a photodetector. It may thereby monitor the perfusion of blood to, for example, the dermis and subcutaneous tissue of the skin. Such perfusion of blood may be modulated by the patient's heartbeat. As another example and not by way of limitation, one or more of the bio-sensors may be electroencephalographic ("EEG") sensors. A health monitoring device 210 may be configured to locally process data gathered by its sensors and determine whether a stopping or discarding condition has occurred. Alternatively, particular embodiments may be deployed as or implemented on a remote device (e.g., a server 140, a mobile electronic device 230) connected, via a network 130, to one or more health monitoring devices 210 each comprising one or more bio-sensors. Such a remote device may receive data from one or more of the connected health monitoring devices 210 and process the received data to determine whether a stopping or discarding condition has occurred.

In particular embodiments, a health monitoring device 210 or a remote device may comprise an application for monitoring a user's health status and a user interface 400 corresponding to the application. As illustrated by FIG. 4A, the user interface 400 may display an indicator 410 (e.g., in the shape of a hand) to indicate that one or more bio-sensors of the device is actively operating to measure one or more biological signals associated with a user of the device. The indicator 410 may disappear if one or more bio-sensors associated with the device is turned off or deactivated. The user interface 400 may comprise one or more fields displaying signals detected by one or more bio-sensors associated with the device. This example user interface 400 may comprise, for example, a field 420 for displaying a detected PPG waveform 425a, a field 430 for displaying a heart rate of the user, a field 440 for displaying a measured stress level of the user, a field 450 for displaying an oxygen level of the user, a field 460 for displaying a respiratory rate of the user, and a field 470 for displaying a number of steps that has been made by the user. The values displayed in the fields 420-470 may be continuously updated in response to new data gathered by one or more bio-sensors associated with the device. FIG. 4B and FIG. 4C illustrate the user interface 400 at two different times. The user interface 400 illustrated by FIG. 4B may display, among other data, a detected PPG waveform 425b. The user interface 400 illustrated by FIG. 4C may display, among other data, a detected PPG waveform 425c. The PPG waveforms 425b and 425c may be different from the PPG waveform 425a. The differences may be caused by differences in the positions of a health monitoring device 210 with respect to the user or differences in noises detected by the health monitoring device 210. As an example and not by way of limitation, the PPG waveform 425b may be created at least in part by an intermittent noise. As another example and not by way of limitation, the PPG waveform 425c may be created at least in part by a temporal absence of eligible signals. Although this disclosure describes particular user interfaces displaying particular signals detected by a health monitoring device in a particular manner, this disclosure contemplates any suitable user interface displaying any suitable signals detected by a health monitoring device in any suitable manner.

Figure 5:
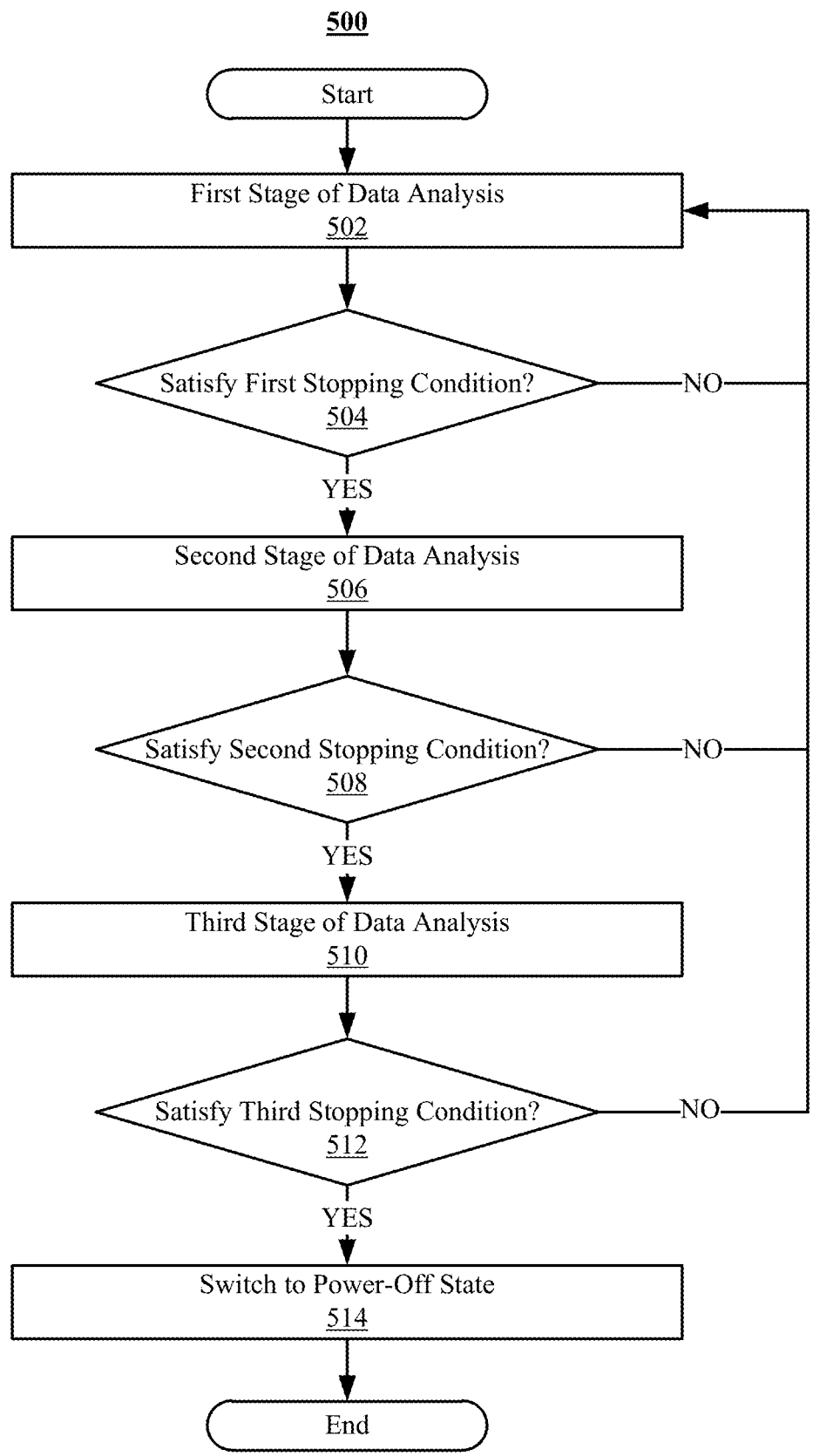
FIG. 5 illustrates an example method 500 for determining whether one or more bio-sensors are sensing live tissues via a multi-stage process.

FIG. 5 illustrates an example method 500 for determining whether one or more bio-sensors are sensing live tissues via a multi-stage process. The method 500 may begin at step 502, where a device associated with a user may perform a first stage of data analysis. This first stage of data analysis may comprise calculating a co-variance of two time-series data collected by one or more bio-sensors associated with the user and comparing the calculated co-variance with a threshold value. At step 504, the device may determine whether a first stopping condition is satisfied. Particular embodiments of steps 502 and 504 are illustrated in greater detail by FIG. 6. If the first stopping condition is determined to not be satisfied at step 504, the device may reinitiate the method 500 by returning to step 502. If the first stopping condition is determined to be satisfied at step 504, the device may proceed to step 506, where it may perform a second stage of data analysis. This second stage of data analysis may comprise comparing a pulsatile amplitude with a non-pulsatile value of a time-series data collected by one or more bio-sensors associated with the user. At step 508, the device may determine whether a second stopping condition is satisfied. Particular embodiments of steps 506 and 508 are illustrated in greater detail by FIG. 7. If the second stopping condition is determined to not be satisfied at step 508, the device may reinitiate the method 500 by returning to step

502. If the second stopping condition is determined to be satisfied at step 508, the device may proceed to step 510, where it may perform a third stage of data analysis. This third stage of data analysis may comprise calculating a MI value between a time-series data collected by one or more bio-sensors and its delayed image. At step 512, the device may determine whether a third stopping condition is satisfied. Particular embodiments of steps 510 and 512 are illustrated in greater detail by FIG. 8. If the third stopping condition is determined to not be satisfied at step 512, the device may reinitiate the method 500 by returning to step 502. If the third stopping condition is determined to be satisfied at step 512, the device may proceed to step 514, where it may switch to a power-off state.

Particular embodiments may repeat one or more steps of the method of FIG. 5, where appropriate. Although this disclosure describes and illustrates particular steps of the method of FIG. 5 as occurring in a particular order, this disclosure contemplates any suitable steps of the method of FIG. 5 occurring in any suitable order. Moreover, although this disclosure describes and illustrates an example method for determining whether one or more bio-sensors are sensing live tissues via a multi-stage process including the particular steps of the method of FIG. 5, this disclosure contemplates any suitable method for determining whether one or more bio-sensors are sensing live tissues via a multi-stage process including any suitable steps, which may include all, some, or none of the steps of the method of FIG. 5, where appropriate. Furthermore, although this disclosure describes and illustrates particular components, devices, or systems carrying out particular steps of the method of FIG. 5, this disclosure contemplates any suitable combination of any suitable components, devices, or systems carrying out any suitable steps of the method of FIG. 5.

In particular embodiments, the method 500 may be implemented such that one or more discarding conditions, rather than one or more of the stopping conditions, are detected. The device, upon detecting one or more of the discarding conditions, may discard data collected by one or more of the bio-sensors associated with the user. In particular embodiments, the method 500 may be implemented such that one or more, rather than all, of the stopping conditions or discarding conditions are required for a stopping or discarding event. More than one stopping condition or discarding condition may be required for a stopping or discarding event to occur at least in part to prevent the occurrence of false alarms. False alarms may be a serious issue in hospital settings because they may result in alarm fatigue (e.g., health care practitioners routinely ignoring alarms). In particular embodiments, a stopping event may comprise turning off the device or switching the device to a power-off state in response to a determination that one or more stopping conditions have occurred. Alternatively or additionally, the stopping event may comprise sending, in response to a determination that one or more stopping conditions have occurred, a signal to one or more sensors associated with the device causing the sensors to stop gathering data. The sensors may or may not be the same sensors whose data are the basis for the determination that one or more stopping conditions have occurred. A sensor may stop gathering data by, for example, switching to a power-off state, stopping receiving signals from its environment, stopping processing or saving any received signal, stopping transmitting data to a remote device configured to process the data, another suitable means of stopping gathering data, or any combination thereof. Alternatively or additionally, the stopping event may comprise terminating one or more other services associated with the device. As an example and not by way of limitation, in response to the determination that one or more stopping conditions have occurred, the device may close a health monitoring application installed on the device, disconnect from a network (e.g., WiFi, 4G), cease transmission of signals (such as sensors data) over a network, or enter into a locked-screen state or a low-power mode. One or more stopping events may be functional to improve a power consumption performance. One or more stopping events may alternatively or additionally be functional to prevent invalid or contaminated data from being collected by one or more bio-sensors associated with the device. As an example and not by way of limitation, a smart watch of a user may determine that the PPG data collected by one or more bio-sensors integrated in the smart watch do not display a waveform consistent with a periodicity caused by the user's heartbeat. It may thereby determine one or more stopping conditions have occurred and infer that it has been taken off from the user's arm wrist. In response, the smart watch may, for example, close an application displaying health status of the user, stop saving signals detected by one or more of PPG sensors, and enter into a locked-screen state to save power.

In particular embodiments, a discarding event may comprise recording time data associated with the determination that one or more discarding conditions have occurred. Specifically, the device may record a present time as soon as it determines that one or more discarding conditions have occurred. Such time data may be stored in one or more data stores 150. The time data may be used as markers for one or more sets of data collected by one or more sensors associated with the device. Such a marker may indicate that any data collected after the recorded time associated with the marker are invalid or of low quality. In particular, such data may be collected when the sensors are not sensing one or more objects that the sensors are configured to sense. Alternatively or additionally, the discarding event may comprise discarding one or more data points collected by one or more sensors associated with the device. The discarded data points may have been collected within a time period defined based at least in part on the recorded time data associated with the discarding condition. Specifically, the device may discard data that have been marked invalid or low-quality based on the recorded time data associated with the determination of one or more discarding conditions. Discarding the data may comprise preventing the data from being saved on a non-transitory storage medium, removing the data from one or more data stores 150, excluding the data from being used for performing health monitoring, measurements, or calculations. One or more discarding events may be functional to protect the integrity of data collected by sensors associated with the device. Continuing the preceding example, the smart watch may further determine that one or more discarding conditions have occurred based on the PPG data. In response, the smart watch may, for example, record a time associated with the determination and discard any PPG data collected after the recorded time.

In particular embodiments, one or more processors associated with the device may be operable to reverse or terminate a stopping or discarding event in response to a triggering event. A triggering event may indicate that a health monitoring device 210 has been re-engaged with a live tissue or otherwise set in a position to detect a suitable and valid signal. The triggering event may comprise, for example, a change in a signal generated by an accelerometer associated with the device, a change in a proximity sensor signal associated with the device, a change in a PPG signal associated with the device, an interaction of a user with the device, another suitable triggering event, or any combination thereof. The device may have caused one or more stopping events or discarding events to occur previously in response to determination that one or more stopping conditions or discarding conditions have occurred. It may then reverse or terminate such stopping or discarding events. As an example and not by way of limitation, in response to the user shaking a health monitoring device 210, a triggering event creating a significant accelerometer reading, one or more processors associated with the device may turn the device back on or switch the device to a power-on state, send a signal to one or more sensors associated with the device to resume gathering data, or resume one or more other services associated with the device. As another example and not by way of limitation, the device may identify and record a time associated with a triggering event, such as a user touching the screen of a smart watch. It may refrain from discarding data that are collected after this recorded time and only discard data collected between the occurrence of one or more discarding events and the triggering event. Although this disclosure describes determining whether one or more bio-sensors are sensing live tissues via a multi-stage process in a particular manner, this disclosure contemplates determining whether one or more bio-sensors are sensing live tissues via a multi-stage process in any suitable manner.

Figure 6:
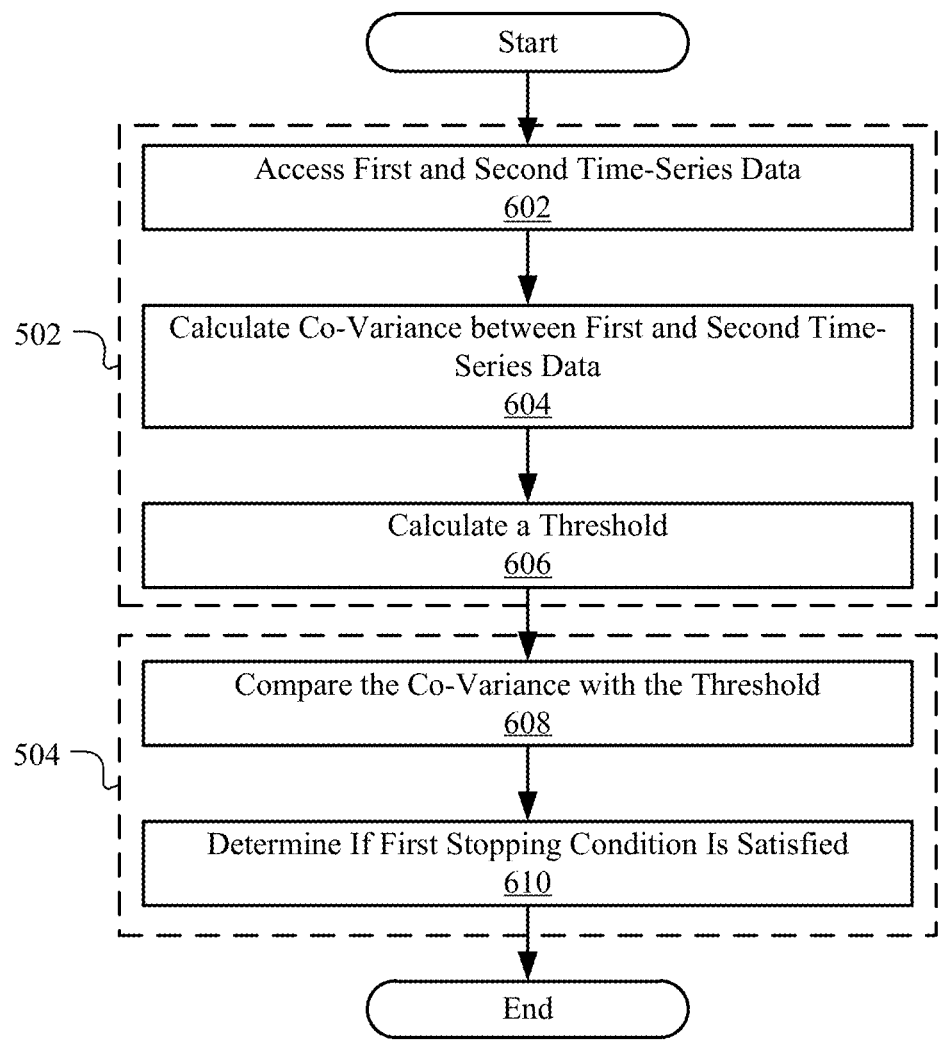
FIG. 6 illustrates an example method 600 for determining if a stopping condition or discarding condition has occurred.

FIG. 6 illustrates an example method 600 for determining if a stopping condition or discarding condition has occurred. The method 600 may begin at step 602, where a device associated with a user may access first time-series data and second time-series data. The first time-series data may be based on electromagnetic radiation in a first spectrum. The second time-series data may be based on electromagnetic radiation in a second spectrum. The first time-series data or the second time-series data may be collected by illuminating a live tissue with electromagnetic radiation in a particular spectrum and detecting electromagnetic radiation passing through or backscattered from the live tissue. As an example and not by way of limitation, the first or second time-series data may be PPG data. The first time-series data may be based on electromagnetic radiation in a red spectrum (e.g., 660 nm). The second time-series data may be based on electromagnetic radiation in an infrared ("IR") spectrum (e.g., 940 nm). The first or second time-series data may alternatively be based on electromagnetic radiation in other spectrums (e.g., green, blue). For collecting PPG data from a human tissue, the red and IR wavelengths, which may fall within the optical window to the human blood, are often chosen so that the corresponding signals sensed at the photodetector can provide the oxygen saturation level of human blood more accurately. Without loss of generality, the first time-series data and the second time-series data, as described hereunder, may refer to time-series data gathered based on red and IR signals, respectively. It is noted that such time-series data may be gathered based on electromagnetic radiation in any other suitable wavelength ranges. The perfusion of blood may be a main modulator that creates periodicity in the collected PPG data. The red and IR wavelengths may be sensitive to the modulation of oxygenated or deoxygenated hemoglobin in human blood. Although each of the red and IR wavelengths may be significantly modulated by both oxygenated and deoxygenated blood, electromagnetic radiation in the red spectrum may be more sensitive to deoxygenated hemoglobin and electromagnetic radiation in the IR spectrum may be more sensitive to oxygenated hemoglobin. The morphology of a PPG waveform generated via a red photodetector and that of a PPG waveform generated via an IR photodetector will be similar (typically the same) in terms of periodicity. But the IR waveform may have a larger amplitude than the red waveform for typical oxygen saturation that is found in the human blood. The first and second time-series data may alternatively be collected by one or more other suitable bio-sensors (e.g., ECG, EEG).

At step 604, the device may compare the first time-series data with the second time-series data. In particular, the device may perform the comparison by calculating a co-variance between the first time-series data and the second time-series data within a specified timeframe. The co-variance of the first time-series data and the second time-series data may be calculated by the following equation:

$$Cov(x_1, x_2) = E[(x_1 - E[x_1])(x_2 - E[x_2])],$$

in which, $x_1$ and $x_2$ may correspond to data points of the first time-series data and the second time-series data, respectively; $E[x]$ may correspond to the expected value of a variable x. Here, the variables $x_1$, $x_2$ and the expected values $E[x_1]$, $E[x_2]$ may each be evaluated within a time period between $t_1$ and $t_2$. As an example and not by way of limitation, the first time-series data or the second time-series data may be PPG data. The PPG signals may be modulated by kinetic movements of blood in a live tissue. The kinetic movements may be similar or identical for different components of the blood (e.g., oxygenated hemoglobin, deoxygenated hemoglobin). This may imply that the amplitude modulation for time-series data generated based on different frequencies of electromagnetic radiation may co-vary closely. This may be true even in the presence of noise generated by turbulence of blood, as induced by mechanical motions of a limb being sensed. Therefore, the co-variance between the first time-series data and the second time-series data may have a high value when the bio-sensors associated with the first and second time-series data are sensing a live tissue with pulsatile blood. On the other hand, the co-variance between the first time-series data and the second time-series data may have a low value when they are results of modulation by random noise when the bio-sensors are not sensing a live tissue. This property of the co-variance between the first time-series data and the second time-series data may be generally true for any detectable periodical biological signal detected by any suitable bio-sensors.

At step 606, the device may calculate a threshold for a co-variance between the first time-series data and the second time-series data. In particular embodiments, the threshold may be a local average co-variance between the first time-series data and the second time-series data. This local average co-variance may be calculated with an exponentially weighted moving average filter. The magnitude of the co-variance between the first time-series data and the second time-series data may be affected by one or more different factors such as, for example, personal characteristics of a user being sensed and positions of one or more bio-sensors with respect to the user. To compare the calculated co-variance with a fixed threshold is one option. But in particular embodiments, it may lead to inaccurate results because the fixed threshold may not be able to account for specific factors related to a specific user or a specific instance of usage. To avoid such risk of inaccurate results, a better option is that the threshold may be set as a local adaptive threshold, which may be obtained by calculating a local average co-variance between the first time-series data and the second time-series data. The local average co-variance may be calculated over a sliding window, which may be a time period with a fixed length that shifts along with the time of measurement. Particular embodiments applying a local adaptive threshold may have superior performance than particular embodiments applying a fixed threshold. Steps 602, 604, and 606 of the example method 600 may correspond to particular embodiments of step 502 of the example method 500.

At step 608, the device may compare the calculated co-variance between the first time-series data and the second time-series data with the calculated threshold value. In particular embodiments, the device may calculate a ratio of a local average co-variance to the co-variance between the first time-series data and the second time-series data within the specified timeframe. This ratio may be associated with an amount of change in the magnitude of the variations of the first and second time-series data over time.

At step 610, the device may determine whether a first stopping condition associated with the device is satisfied based on the comparison of the first time-series data and the second time-series data. In particular, the device may determine whether the first stopping condition has occurred by determining whether the calculated ratio changes by a magnitude (e.g., in decibels) that is greater than a threshold magnitude. A significant change in the ratio may indicate a disappearance of a source of modulation of the signals (e.g., the kinetic movement of blood due to heartbeat) or an existence of significant noise. Such an indication may suggest the data collected by one or more bio-sensors are no longer valid or reliable. The device may thereby determine that a stopping condition or a discarding condition has occurred. Steps 608 and 610 of the example method 600 may correspond to particular embodiments of step 504 of the example method 500.

In particular embodiments, the device may alternatively or additionally calculate a variance of the first time-series data or the second time-series data within a specified timeframe. The variance may be calculated using the following equation:

$$\mathrm{Var}(x) = E[(x - E[x])^2],$$

in which, x may correspond to data points of a set of time-series data; E[x] may correspond to the expected value of a variable x. Here, the variable x and the expected value E[x] may each be evaluated within a time period between $t_1$ and $t_2$. The variance of the data may increase with the dynamics of one or more periodical biological signals of a human body (e.g., pulse pressure wave as a result of blood flow). The device may compare the calculated variance with a local adaptive threshold in a manner similar to that of method 600 to determine whether a stopping condition or a discarding condition has occurred.

Particular embodiments may repeat one or more steps of the method of FIG. 6, where appropriate. Although this disclosure describes and illustrates particular steps of the method of FIG. 6 as occurring in a particular order, this disclosure contemplates any suitable steps of the method of FIG. 6 occurring in any suitable order. Moreover, although this disclosure describes and illustrates an example method for determining if a stopping condition or discarding condition has occurred including the particular steps of the method of FIG. 6, this disclosure contemplates any suitable method for determining if a stopping condition or discarding condition has occurred including any suitable steps, which may include all, some, or none of the steps of the method of FIG. 6, where appropriate. Furthermore, although this disclosure describes and illustrates particular components, devices, or systems carrying out particular steps of the method of FIG. 6, this disclosure contemplates any suitable combination of any suitable components, devices, or systems carrying out any suitable steps of the method of FIG. 6.

Figure 7:
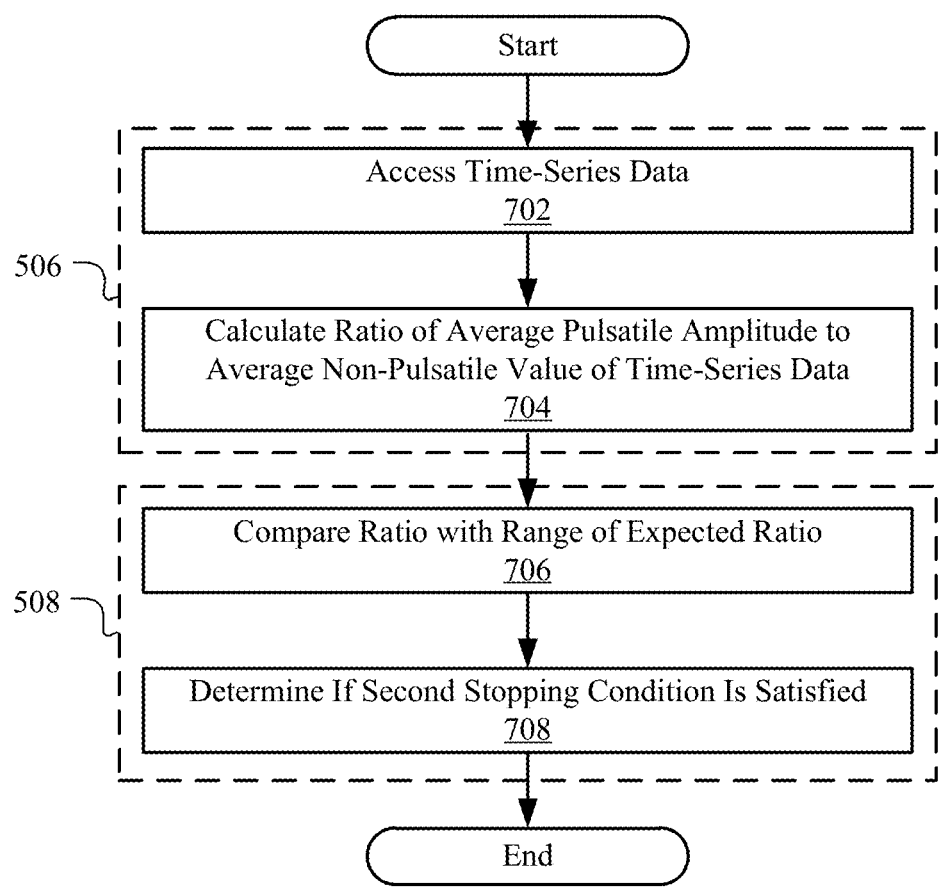
FIG. 7 illustrates an example method 700 for determining if a stopping condition or discarding condition has occurred.

FIG. 7 illustrates an example method 700 for determining if a stopping condition or discarding condition has occurred. The method 700 may begin at step 702, where a device associated with a user may access time-series data. The time-series data may be based on electromagnetic radiation in a particular spectrum. Continuing the preceding examples, the time-series data may be PPG data obtained with light in the red or IR spectrum. The PPG signal may be modulated by perfusion of blood in a live tissue sensed by a bio-sensor and have a periodicity associated with the user's heartbeat. The PPG signal may therefore have a pattern of a pulse pressure wave. In presence of a heartbeat, the pulsatile amplitude of the PPG signal may represent pulsation of arterial blood of the user. The non-pulsatile value of the PPG signal may represent the non-pulsatile component of the blood which includes non-pulsatile arterial blood and venous blood. Such non-pulsatile value may further represent absorption of background tissues of the user being sensed (e.g., bones, cartilage, extra-cellular fluids).

At step 704, the device may calculate a ratio of an average pulsatile amplitude to an average non-pulsatile value of the time-series data within a specified timeframe. Then, at step 706, the device may compare the calculated ratio with a range of expected ratio. The range of expected ratio may be determined based on empirical physiological studies on the human body. As an example and not by way of limitation, the expected ratio between the pulsatile component and the non-pulsatile component of PPG signal in presence of live human tissue may be set as between 0.1 and 0.01. On the other hand, the ratio between the pulsatile component and the non-pulsatile component may not fall within such a range if the bio-sensor is instead sensing an inert surface. At step 708, the device may determine whether a second stopping condition is satisfied based on the comparison at step 706. If the calculated ratio does not fall in the range of expected ratio for live tissue, the device may determine that a live tissue is not in presence and that a stopping condition or a discarding condition has occurred. Steps 702 and 704 of the example method 700 may correspond to particular embodiments of step 506 of the example method 500. Steps 706 and 708 of the example method 700 may correspond to particular embodiments of step 508 of the example method 500.

Particular embodiments may repeat one or more steps of the method of FIG. 7, where appropriate. Although this disclosure describes and illustrates particular steps of the method of FIG. 7 as occurring in a particular order, this disclosure contemplates any suitable steps of the method of FIG. 7 occurring in any suitable order. Moreover, although this disclosure describes and illustrates an example method for determining if a stopping condition or discarding condition has occurred including the particular steps of the method of FIG. 7, this disclosure contemplates any suitable method for determining if a stopping condition or discarding condition has occurred including any suitable steps, which may include all, some, or none of the steps of the method of FIG. 7, where appropriate. Furthermore, although this disclosure describes and illustrates particular components, devices, or systems carrying out particular steps of the method of FIG. 7, this disclosure contemplates any suitable combination of any suitable components, devices, or systems carrying out any suitable steps of the method of FIG. 7.

Figure 8:
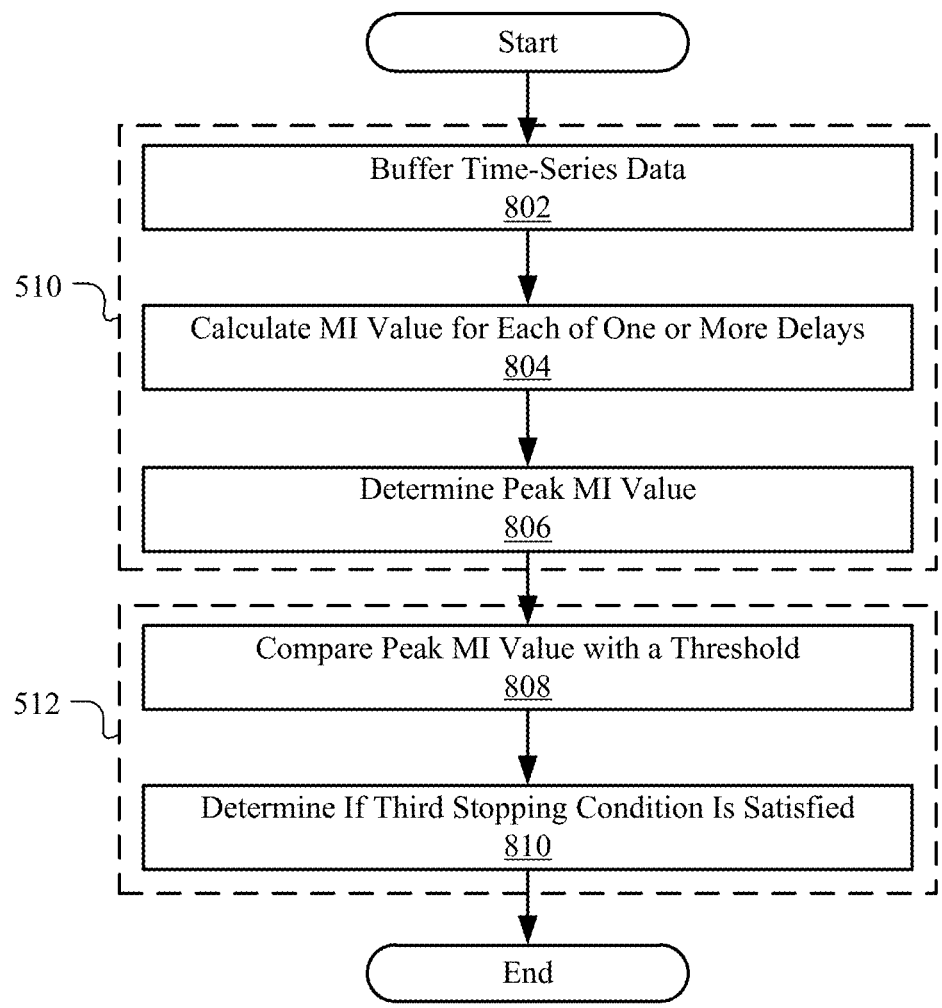
FIG. 8 illustrates an example method 800 for determining if a stopping condition or discarding condition has occurred.

FIG. 8 illustrates an example method 800 for determining if a stopping condition or discarding condition has occurred. The method 800 may begin at step 802, where a device associated with a user may buffer time-series data. The time-series data may be collected by a bio-sensor configured to detect a periodical biological signal. The device may buffer one or more sets of time-series data corresponding to one or more different time windows. The length of a time window may be determined based on an approximate period of the biological signal that the bio-sensor is configured to detect and one or more periods of one or more periodical biological activities that are sources of noise. As an example and not by way of limitation, for a bio-sensor configured to detect a biological signal modulated by a user's heartbeat, the device may choose a time window of a length that is longer than a period of an ordinary person's heartbeat but shorter than a period of an ordinary person's respiratory sinus arrhythmia ("RSA") cycle, which may be a heart rate variability in synchrony with respiration. Such a time window may be long enough for the device to buffer enough data for the detection of specific frequency-components-of-interest (e.g., heart rate) while also short enough to avoid gradual periodicity drift due to noise (e.g., RSA). In particular embodiments, the device may apply one or more filters (e.g., detrending filter, low-pass filter. high-pass filter) to the buffered time-series data before analyzing such data to determine whether a stopping condition or discarding condition has occurred.

At step 804, the device may calculate a MI value between the time-series data and a delayed image of the time-series data associated with each of one or more different delays. A delayed image of a set of time-series data buffered by the device may be generated by adding a time delay to each data point in the set. A MI value between a set of data and a delayed image of the data may be interpreted to provide an average amount of information a given measurement X(t) gives about another, delayed, measurement X(t+τ), where τ represents a time delay. The MI value may be calculated based on the following equation:

$$MI(\tau) = \sum_{x(t), x(t+\tau)} P(x(t), x(t+\tau)) \log \frac{P(x(t), x(t+\tau))}{P(x(t))P(x(t+\tau))},$$

where x(t) may correspond to a random variable associated with a set of time-series data buffered by the device; x(t+τ) may correspond to a random variable associated with a delayed image of the set of time-series data; P(x(t), x(t+τ)) may be a joint probability distribution function of the variables x(t) and x(t+τ); P(x(t)) and P(x(t+τ)) may be marginal probability distribution functions of the variables x(t) and x(t+τ) respectively. In particular embodiments, a MI value between data collected based on a periodical signal and a delay image of the signal may generally be larger than its counterpart for a non-periodical signal.

In particular embodiments, the device may create an array containing a set of time-series data $\hat{X}$:x(t). The time-series data in the array may be normalized. As an example and not by way of limitation, the data may be normalized by subtracting the minimum value from each data point and dividing each data point by the then maximum value:

$$x^*(t) = \frac{x(t) - x_{min}}{x_{max} - x_{min}}.$$

The device may then create L delayed images $\hat{Y}$:x(t+τ) of the data array by adding a time delay τ to each data point included in the array, where τ ranges from 1 to L (the unit is Δt, which is a length of time between two consecutive samplings by a bio-sensor). The device may then calculate a MI value between each delayed image of the data array and the original data array. For calculating the MI value, the first τ data points of the time-series data $\hat{X}$ and the last τ data points of the delayed image $\hat{Y}$ may be removed such that both data array have the same length and both are within the original time window. The calculation of the MI value may be calculated based on a delayed-phase portrait $\hat{X}\hat{Y}$ associated with the data array and its delayed image. The delayed-phase portrait $\hat{X}\hat{Y}$ may comprise two time axes corresponding to the data array $\hat{X}$ and its delayed image $\hat{Y}$, respectively. Each axis of the delayed-phase portrait $\hat{X}\hat{Y}$ may be partitioned in to a number (n) of bins using a binning algorithm. The delayed-phase portrait may thereby be divided into $n^2$ box partitions. The number n may be dynamically or periodically adjusted to optimize the performance and accuracy of this method of detecting a stopping or discarding condition. The optimization may involve balancing high accuracy associated with a small n and ability to handle small time delays τ (i.e., a high resolution) associated with a large n. In particular embodiments, the binning algorithm may be improved to include adaptive binning that is non-constant for regions of the phase space. The adaptive binning may be based on a point density associated with the delayed-phase portrait. For this improved algorithm, a bin size constant may be calculated by the following equation:

$$n = \left\lfloor 1 + \log_2(N - \tau) + \frac{1}{2} \right\rfloor,$$

where, N corresponds to a number of data points in each data array $\hat{X}$ and $\hat{Y}$.

In particular embodiments, the device may check for a constant or approximately constant signal based on the time-series data x(t). Specifically, the device may calculate a variance Var(x(t)) of the time-series data x(t) and determine whether the variance Var(x(t)) is sufficiently close to zero or smaller than a threshold value. If so, the device may directly determine that the time-series data x(t) or its corresponding signal shows no periodical behavior corresponding to a living tissue. The co-variance values and MI values between the time series data x(t) and delayed versions of such data would be trivially small. This determination may obviate the need to calculate the MI values associated with the time-series data x(t). The device may thereby determine that a stopping condition or discarding condition has occurred. On the other hand, if the variance Var(x(t)) is determined to be larger than the threshold value, the device may proceed to the remaining steps in calculating the MI values, as discussed below. As the calculation of the MI values may be demanding with respect to time and processing power, this intermediate checking step may improve the efficiency of the example method 800 by preventing unnecessary calculations of MI values.

In particular embodiments, the device may define box-search variables $s_1$ and $s_2$, where $s_1$ is associated with a partition along an inner vertical axis of the delayed-phase portrait $\hat{X}\hat{Y}$ and $s_2$ is associated with a partition along an inner horizontal axis of the delayed-phase portrait $\hat{X}\hat{Y}$. Each box on the delayed-phase portrait $\hat{X}\hat{Y}$ may correspond to a point $(s_{1_i}, s_{2_j})$, where i and j ranges from 1 to n. Defining the box-search variables for the delayed-phase portrait corresponding to different time delays τ may be implemented using a nested for-loop algorithm.

In particular embodiments, the device may define probability distributions $p$, $p_x$, $p_y$, which correspond to joint probability distribution of $\hat{X}$ and $\hat{Y}$, probability distribution of $\hat{X}$, and probability distribution of $\hat{Y}$, respectively. The device may further define the following conditions:

$C_1: \frac{s_{1_i} - 1}{n} < x_k, \{k = 1, 2, \ldots, n - \tau\};$ $C_2: \frac{s_{1_i}}{n} \geq x_k, \{k = 1, 2, \ldots, n - \tau\};$ $C_3: \frac{s_{2_j} - 1}{n} < x_k, \{k = 1 + \tau, 2 + \tau, \ldots, n\};$ $C_4: \frac{s_{2_j}}{n} \geq x_k, \{k = 1 + \tau, 2 + \tau, \ldots, n\};$ $C_{s_{1_i}, s_{2_j}} = 1$ if $C_1$, $C_2$, $C_3$, and $C_4$ are true;

$G_{s_{1_i}, s_{2_j}} = 1$ if $C_1$ and $C_2$ are true;

$F_{s_{1_i}, s_{2_j}} = 1$ if $C_3$ and $C_4$ are true.

Based on the above conditions, the probability distributions may be defined as:

$$p = \frac{\sum_{s_{1_i}=1}^{n} \sum_{s_{2_j}=1}^{n} C_{s_{1_i}, s_{2_j}}}{N - \tau};$$

$$p_x = \frac{\sum_{s_{1_i}=1}^{n} \sum_{s_{2_j}=1}^{n} G_{s_{1_i}, s_{2_j}}}{N - \tau};$$

$$p_y = \frac{\sum_{s_{1_i}=1}^{n} \sum_{s_{2_j}=1}^{n} F_{s_{1_i}, s_{2_j}}}{N - \tau}.$$

In particular embodiments, the MI value between original time-series data and a delayed image corresponding to a time delay τ may then be calculated as follows:

$$MI(\tau) = \sum_k p \cdot \log \frac{p}{p_x p_y}.$$

Note that this equation may be equivalent to the equation described above:

$$MI(\tau) = \sum_{x(t), x(t+\tau)} P(x(t), x(t+\tau)) \log \frac{P(x(t), x(t+\tau))}{P(x(t)) P(x(t+\tau))}.$$

The MI values corresponding to all values of the time delay τ may be calculated as described above and aggregated into an MI array. The MI values in the MI array may be ordered based on their corresponding τ values.

At step 806, the device may determine a peak MI value corresponding to a particular delay. In particular embodiments, the MI value may be relatively high for a small time delay τ due to the closeness of the times of measurements. This may be consistent with the interpretation that x(t) gives much information about x(t+τ) when τ is small. The MI value may decrease as τ increases and as the information x(t) gives about x(t+τ) decreases. In particular embodiments, the MI value may decrease as τ increases until the time delay τ gets close to a periodicity of the time-series data if such periodicity exists. The MI value may reach a local peak at a τ corresponding to a period (or approximate period) of the time-series data. As an example and not by way of limitation, a PPG data may be substantially modulated by a user's heartbeat. A MI value between this PPG data and its delayed images may exhibit a local peak at a time delay τ corresponding to a period of the user's heartbeat. A frequency transform of this peak time delay τ may correspond to a heart rate of the user. In particular embodiments, the device may read the MI array and determine a height of and a time delay τ associated with a local peak of the MI array.

At step 808, the device may compare the determined peak MI value with a threshold MI value. In particular embodiments, the threshold MI value may be associated with a local peak of an array of local average MI values associated with one or more prior time windows. In particular embodiments, the device may access time-series data associated with multiple different time-windows and buffer the accessed time-series data. It may then repeat step 804 multiple times to calculate multiple MI arrays. The device may compute an array of local adaptive average MI values for one or more sets of time-series data associated with one or more different time windows. As an example and not by way of limitation, the device may aggregate three separate sets of MI calculations as follows:

$$MI^*(\tau) = \frac{MI_1(\tau) + MI_2(\tau) + MI_3(\tau)}{3}.$$

The array $MI^*(\tau)$ may be an average of three previous MI arrays $MI_1(\tau)$, $MI_2(\tau)$, and $MI_3(\tau)$. The device may then identify a local peak of the array $MI^*(\tau)$ and use this value as a threshold. The device may then compare a peak value of an MI array $MI_0(\tau)$ corresponding to a most recently buffered time-series data set with this threshold.

In particular embodiments, the device may alternatively compute an array of sum MI values for one or more sets of time-series data associated with one or more different time windows. As an example and not by way of limitation, the device may aggregate four separate sets of MI calculations as follows:

$$MI^{**}(\tau) = MI_0(\tau) + MI_1(\tau) + MI_2(\tau) + MI_3(\tau).$$

The array $MI^{}(\tau)$ may be a sum of a most recent MI array $MI_0(\tau)$ and three previous MI arrays $MI_1(\tau)$, $MI_2(\tau)$, and $MI_3(\tau)$. In particular embodiments, the sum MI array $MI^{}(\tau)$ may be calculated based on a sliding time window. When a new set of time-series data associated with a new time window becomes available, the device may remove an oldest set of time-series data from its buffer to make space for this new set of time-series data. It also may remove the oldest MI array (e.g., $MI_3(\tau)$) in the equation for calculating the sum MI array, shift each remaining MI array in the equation one position up (e.g., change $MI_2(\tau)$ to $MI_3(\tau)$, change $MI_0(\tau)$ to $MI_1(\tau)$), and add the newest MI array as a term of the summation (e.g., the newest MI array becoming $MI_0(\tau)$). The device may then identify a local peak in the sum MI array MI**(τ) and compare it with a peak value of a previously calculated sum MI array to determine an amount of change.

At step 810, the device may determine if a third stopping condition is satisfied. In particular embodiments, the peak MI value for a signal with strong periodicity is likely to be large. Based on the comparisons at step 808, if a peak MI value for a most recent set of time-series data is substantially smaller than a threshold MI value or the addition of a new MI array substantially reduces the value of a peak of the sum MI array, the device may determine that the signal has lost its periodicity. For a bio-sensor configured to detect a signal modulated by a periodical biological signal (e.g., signal from heartbeat), the device may determine that the bio-sensor is no longer sensing a live tissue based on the loss of periodicity in its signals. It may thereby determine that a stopping condition or discarding condition has occurred. Steps 802, 804, and 806 of the example method 800 may correspond to particular embodiments of step 510 of the example method 500. Steps 808 and 810 of the example method 800 may correspond to particular embodiments of step 512 of the example method 500.

Particular embodiments may repeat one or more steps of the method of FIG. 8, where appropriate. Although this disclosure describes and illustrates particular steps of the method of FIG. 8 as occurring in a particular order, this disclosure contemplates any suitable steps of the method of FIG. 8 occurring in any suitable order. Moreover, although this disclosure describes and illustrates an example method for determining if a stopping condition or discarding condition has occurred including the particular steps of the method of FIG. 8, this disclosure contemplates any suitable method for determining if a stopping condition or discarding condition has occurred including any suitable steps, which may include all, some, or none of the steps of the method of FIG. 8, where appropriate. Furthermore, although this disclosure describes and illustrates particular components, devices, or systems carrying out particular steps of the method of FIG. 8, this disclosure contemplates any suitable combination of any suitable components, devices, or systems carrying out any suitable steps of the method of FIG. 8.

In particular embodiments, the example methods 600, 700, and 800 may be associated with different approaches for determining whether a stopping condition or discarding conditions has occurred based on detection of a same periodical biological signal. Their combination may bring particular advantages. The approach based on calculating co-variances or variances of time-series data (as illustrated by FIG. 6) may be capable of rapid detection (e.g., on the magnitude of tenths of milliseconds) of disturbances for data collection such as, for example, poor finger placement or placement on objects that are not live tissues. It may be particularly useful for the identification of small time-scale perturbations that may lead to episodic corruption of bio-signals. This approach may be particularly suitable for identifying and discarding invalid or corrupted data. The approach based on calculating MI values between time-series data and corresponding delayed images (as illustrated by FIG. 8) may require computation over large timescales (e.g., on the magnitude of seconds) and may be sensitive to prolonged absences of pulsation. This approach may be resilient to the risk of false alarm based on brief perturbations (e.g., finger-placement noise) or intermittent noise to the bio-signal. It may be particularly suitable as an indicator for turning off a health monitoring device 210 to conserve power. The approach based on comparing a pulsatile amplitude and a non-pulsatile value of a set of time-series data (as illustrated by FIG. 7) may require a small amount of storage space and processing power. It may be particularly efficient to implement.

Figure 9:
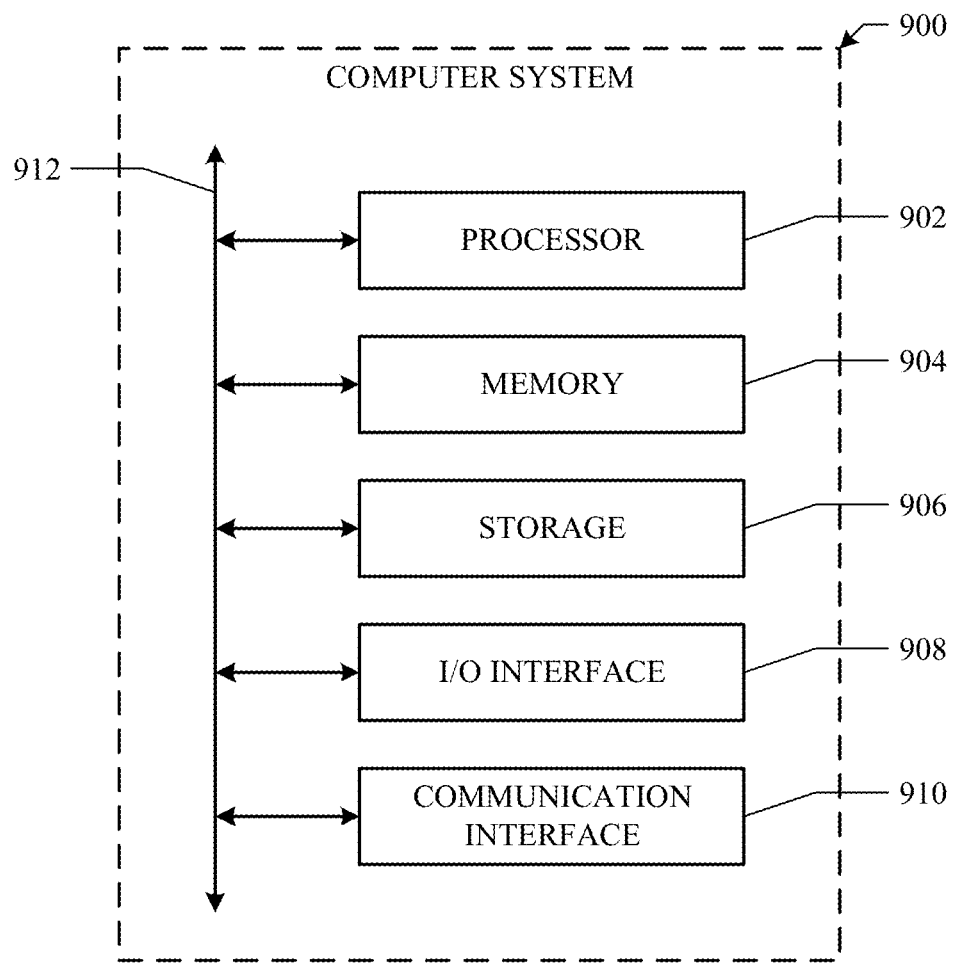
FIG. 9 illustrates an example computer system according to particular embodiments of the invention.

FIG. 9 illustrates an example computer system 900 according to some embodiments of the invention. In particular embodiments, one or more computer systems 900 perform one or more steps of one or more methods described or illustrated herein. In particular embodiments, one or more computer systems 900 provide functionality described or illustrated herein. In particular embodiments, software running on one or more computer systems 900 performs one or more steps of one or more methods described or illustrated herein or provides functionality described or illustrated herein. Particular embodiments include one or more portions of one or more computer systems 900. Herein, reference to a computer system may encompass a computing device, and vice versa, where appropriate. Moreover, reference to a computer system may encompass one or more computer systems, where appropriate.

This disclosure contemplates any suitable number of computer systems 900. This disclosure contemplates computer system 900 taking any suitable physical form. As example and not by way of limitation, computer system 900 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 900 may include one or more computer systems 900; be unitary or distributed; span multiple locations; span multiple machines; span multiple data centers; or reside in a cloud, which may include one or more cloud components in one or more networks. Where appropriate, one or more computer systems 900 may perform without substantial spatial or temporal limitation one or more steps of one or more methods described or illustrated herein. As an example and not by way of limitation, one or more computer systems 900 may perform in real time or in batch mode one or more steps of one or more methods described or illustrated herein. One or more computer systems 900 may perform at different times or at different locations one or more steps of one or more methods described or illustrated herein, where appropriate.

In particular embodiments, computer system 900 includes a processor 902, memory 904, storage 906, an input/output (I/O) interface 908, a communication interface 910, and a bus 912. Although this disclosure describes and illustrates a particular computer system having a particular number of particular components in a particular arrangement, this disclosure contemplates any suitable computer system having any suitable number of any suitable components in any suitable arrangement.

In particular embodiments, processor 902 includes hardware for executing instructions, such as those making up a computer program. In particular embodiments, the computer program causes the processor 902 to perform one or more steps of one or more methods described or illustrated herein or provides functionality described or illustrated herein. In this way, the processor 902 coupled to the computer program is a special purpose processor for performing the functions defined by the computer program. As an example and not by way of limitation, to execute instructions, processor 902 may retrieve (or fetch) the instructions from an internal register, an internal cache, memory 904, or storage 906; decode and execute them; and then write one or more results to an internal register, an internal cache, memory 904, or storage 906. In particular embodiments, processor 902 may include one or more internal caches for data, instructions, or addresses. This disclosure contemplates processor 902 including any suitable number of any suitable internal caches, where appropriate. As an example and not by way of limitation, processor 902 may include one or more instruction caches, one or more data caches, and one or more translation lookaside buffers (TLBs). Instructions in the instruction caches may be copies of instructions in memory 904 or storage 906, and the instruction caches may speed up retrieval of those instructions by processor 902. Data in the data caches may be copies of data in memory 904 or storage 906 for instructions executing at processor 902 to operate on; the results of previous instructions executed at processor 902 for access by subsequent instructions executing at processor 902 or for writing to memory 904 or storage 906; or other suitable data. The data caches may speed up read or write operations by processor 902. The TLBs may speed up virtual-address translation for processor 902. In particular embodiments, processor 902 may include one or more internal registers for data, instructions, or addresses. This disclosure contemplates processor 902 including any suitable number of any suitable internal registers, where appropriate. Where appropriate, processor 902 may include one or more arithmetic logic units (ALUs); be a multi-core processor; or include one or more processors 902. Although this disclosure describes and illustrates a particular processor, this disclosure contemplates any suitable processor.

In particular embodiments, memory 904 includes main memory for storing instructions for processor 902 to execute or data for processor 902 to operate on. As an example and not by way of limitation, computer system 900 may load instructions from storage 906 or another source (such as, for example, another computer system 900) to memory 904. Processor 902 may then load the instructions from memory 904 to an internal register or internal cache. To execute the instructions, processor 902 may retrieve the instructions from the internal register or internal cache and decode them. During or after execution of the instructions, processor 902 may write one or more results (which may be intermediate or final results) to the internal register or internal cache. Processor 902 may then write one or more of those results to memory 904. In particular embodiments, processor 902 executes only instructions in one or more internal registers or internal caches or in memory 904 (as opposed to storage 906 or elsewhere) and operates only on data in one or more internal registers or internal caches or in memory 904 (as opposed to storage 906 or elsewhere). One or more memory buses (which may each include an address bus and a data bus) may couple processor 902 to memory 904. Bus 912 may include one or more memory buses, as described below. In particular embodiments, one or more memory management units (MMUs) reside between processor 902 and memory 904 and facilitate accesses to memory 904 requested by processor 902. In particular embodiments, memory 904 includes random access memory (RAM). This RAM may be volatile memory, or may be dynamic RAM (DRAM) or static RAM (SRAM). Moreover, where appropriate, this RAM may be single-ported or multi-ported RAM. This disclosure contemplates any suitable RAM. Memory 904 may include one or more memories 904, where appropriate. Although this disclosure describes and illustrates particular memory, this disclosure contemplates any suitable memory.

In particular embodiments, storage 906 includes mass storage for data or instructions. As an example and not by way of limitation, storage 906 may include a hard disk drive (HDD), a floppy disk drive, flash memory, an optical disc, a magneto-optical disc, magnetic tape, or a Universal Serial Bus (USB) drive or a combination of two or more of these. Storage 906 may include removable or non-removable (or fixed) media, where appropriate. Storage 906 may be internal or external to computer system 900, where appropriate. In particular embodiments, storage 906 is non-volatile, solid-state memory. In particular embodiments, storage 906 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 906 taking any suitable physical form. Storage 906 may include one or more storage control units facilitating communication between processor 902 and storage 906, where appropriate. Where appropriate, storage 906 may include one or more storages 906. Although this disclosure describes and illustrates particular storage, this disclosure contemplates any suitable storage.

In particular embodiments, I/O interface 908 includes hardware, software, or both, providing one or more interfaces for communication between computer system 900 and one or more I/O devices. Computer system 900 may include one or more of these I/O devices, where appropriate. One or more of these I/O devices may enable communication between a person and computer system 900. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 908 for them. Where appropriate, I/O interface 908 may include one or more device or software drivers enabling processor 902 to drive one or more of these I/O devices. I/O interface 908 may include one or more I/O interfaces 908, where appropriate. Although this disclosure describes and illustrates a particular I/O interface, this disclosure contemplates any suitable I/O interface.

In particular embodiments, communication interface 910 includes hardware, software, or both providing one or more interfaces for communication (such as, for example, packet-based communication) between computer system 900 and one or more other computer systems 900 or one or more networks. As an example and not by way of limitation, communication interface 910 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 910 for it. As an example and not by way of limitation, computer system 900 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 900 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 900 may include any suitable communication interface 910 for any of these networks, where appropriate. Communication interface 910 may include one or more communication interfaces 910, where appropriate. Although this disclosure describes and illustrates a particular communication interface, this disclosure contemplates any suitable communication interface.

In particular embodiments, bus 912 includes hardware, software, or both coupling components of computer system 900 to each other. As an example and not by way of limitation, bus 912 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 912 may include one or more buses 912, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. A system comprising: a non-transitory computer-readable memory comprising instructions; and one or more processors coupled to the memory and operable to execute the instructions to:

access first time-series data based on electromagnetic radiation in a first spectrum detected by one or more sensors of a wearable computing device;

access second time-series data based on electromagnetic radiation in a second spectrum detected by the one or more sensors of the wearable computing device;

compare the first time-series data with the second time-series data;

determine, based on the comparison:

whether a stopping condition associated with the wearable device has occurred; or whether a discarding condition associated with the first time-series data or the second time-series data has occurred; and either in response to a determination that the stopping condition associated with the client computing device has occurred, generate an instruction to reduce a power level of a bio-sensor of the wearable computing device; or in response to a determination that a discarding condition associated with the first time-series data or the second time-series data has occurred, generate an instruction to discard at least some data gathered by the bio-sensor of the client computing device.

2. The system of claim 1, wherein the wearable device comprises:

a mobile phone;
   a smart watch;
   a fitness tracker;
   a wristband;
   a necklace;
   a head-worn device;
   a piece of clothing;
   a ring; or
   a chest drape.

3. The system of claim 1, wherein the wearable device comprises:

the non-transitory computer-readable memory;
   the one or more processors; and
   a first sensor configured to:
   detect the electromagnetic radiation in the first spectrum, and
   generate the first time-series data based on the detected electromagnetic radiation.

4. The system of claim 1, wherein the first time-series data or the second time-series data comprise photoplethysmographic ("PPG") data.

5. The system of claim 1, wherein the one or more processors are further operable to execute the instructions to:

calculate a variance for the first time-series data within a specified timeframe; or calculate a variance for the second time-series data within a specified timeframe.

6. The system of claim 1, wherein the one or more processors operable to execute the instructions to compare the first time-series data with the second time-series data comprise one or more processors operable to execute the instructions to calculate a co-variance between the first time-series data and the second time-series data within a specified timeframe.

7. The system of claim 6, wherein the one or more processors operable to execute the instructions to determine whether the stopping condition or the discarding condition has occurred comprise one or more processors operable to execute the instructions to:

calculate a local average co-variance between the first time-series data and the second time-series data, wherein the local average co-variance is calculated with an exponentially weighted moving average filter;

calculate a ratio of the local average co-variance to the co-variance between the first time-series data and the second time-series data within the specified timeframe; and determine whether the calculated ratio changes by a magnitude that is greater than a threshold magnitude.

8. The system of claim 1, wherein the one or more processors are further operable to execute the instructions to:

calculate a ratio of an average pulsatile amplitude associated with the first set of time series data to an average non-pulsatile value of the first set of time series data within a specified timeframe; and determine whether the stopping condition or the discarding condition occurs by comparing the calculated ratio with a range of expected ratio.

9. The system of claim 1, wherein the one or more processors are further operable to execute the instructions to:

calculate a mutual information ("MI") value between the first time-series data and a delayed image of the first time-series data within a specified timeframe, wherein the delayed image is generated by adding a delay to each data point of the first time-series data; and determine whether the stopping condition or the discarding condition has occurred by comparing the calculated MI value with a threshold MI value.

10. The system of claim 9, wherein the delay is based on a heart rate of a user of the device.

11. The system of claim 1, wherein the one or more processors are further operable to execute the instructions to turn off the device in response to a determination that the stopping condition has occurred.

12. The system of claim 1, wherein the instruction to reduce a power level of the bio-sensor comprises an instruction for the bio-sensor to stop gathering data.

13. The system of claim 1, wherein the one or more processors are further operable to execute the instructions to record time data associated with the determination that the discarding condition has occurred.

14. The system of claim 13, wherein the one or more processors are further operable to execute the instructions to discard one or more data points associated with the first time-series data or the second time-series data, wherein the discarded data points were collected by the bio-sensor within a time period defined based at least in part on the recorded time data associated with the discarding condition.

15. The system of claim 1, wherein the one or more processors are further operable to execute the instructions to turn on the wearable computing device in response to a triggering event, wherein the triggering event comprises:

a change in a signal generated by an accelerometer associated with the wearable computing device;

a change in a proximity sensor signal associated with the wearable computing device;

a change in a PPG signal associated with the wearable computing device; or an interaction of a user with the wearable computing device.

16. One or more computer-readable non-transitory storage media embodying software that is operable when executed by a processor to:

access first time-series data based on electromagnetic radiation in a first spectrum detected by one or more sensors of a wearable computing device;

access second time-series data based on electromagnetic radiation in a second spectrum detected by the one or more sensors of the wearable computing device;

compare the first time-series data with the second time-series data;

determine, based on the comparison:

whether a stopping condition associated with the wearable device has occurred; or whether a discarding condition associated with the first time-series data or the second time-series data has occurred; and either in response to a determination that the stopping condition associated with the client computing device has occurred, generate an instruction to reduce a power level of a bio-sensor of the wearable computing device; or in response to a determination that a discarding condition associated with the first time-series data or the second time-series data has occurred, generate an instruction to discard at least some data gathered by the bio-sensor of the client computing device.

17. The media of claim 16, wherein the software is further operable when executed by the processor to:

calculate a variance for the first time-series data within a specified timeframe; or calculate a variance for the second time-series data within a specified timeframe.

18. The media of claim 16, wherein the software that is operable when executed by the processor to compare the first time-series data with the second time-series data comprises software that is operable when executed by the processor to calculate a co-variance between the first time-series data and the second time-series data within a specified timeframe.

19. The media of claim 18, wherein the software that is operable when executed by the processor to determine whether the stopping condition or the discarding condition has occurred comprises software that is operable when executed by the processor to:

calculate a local average co-variance between the first time-series data and the second time-series data, wherein the local average co-variance is calculated with an exponentially weighted moving average filter;

calculate a ratio of the local average co-variance to the co-variance between the first time-series data and the second time-series data within the specified timeframe; and determine whether the calculated ratio changes by a magnitude that is greater than a threshold magnitude.

20. The media of claim 16, wherein the software is further operable when executed by the processor to:
- calculate a ratio of an average pulsatile amplitude associated with the first set of time series data to an average non-pulsatile value of the first set of time series data within a specified timeframe; and
- determine whether the stopping condition or the discarding condition occurs by comparing the calculated ratio with a range of expected ratio.

21. The media of claim 16, wherein the software is further operable when executed by the processor to:
- calculate a mutual information ("MI") value between the first time-series data and a delayed image of the first time-series data within a specified timeframe, wherein the delayed image is generated by adding a delay to each data point of the first time-series data; and
- determine whether the stopping condition or the discarding condition has occurred by comparing the calculated MI value with a threshold MI value.

22. A method comprising, by one or more computing devices:
- accessing first time-series data based on electromagnetic radiation in a first spectrum detected by one or more sensors of a wearable computing device;
- accessing second time-series data based on electromagnetic radiation in a second spectrum detected by the one or more sensors of the wearable computing device;
- comparing the first time-series data with the second time-series data; and
- determining, based on the comparison:
  - whether a stopping condition associated with the wearable device has occurred; or
  - whether a discarding condition associated with the first time-series data or the second time-series data has occurred; and
- either
  - in response to a determination that the stopping condition associated with the client computing device has occurred, generating an instruction to reduce a power level of a bio-sensor of the wearable computing device; or
  - in response to a determination that a discarding condition associated with the first time-series data or the second time-series data has occurred, generating an instruction to discard at least some data gathered by the bio-sensor of the client computing device.

23. The method of claim 22, further comprising:
- calculating a variance for the first time-series data within a specified timeframe; or
- calculating a variance for the second time-series data within a specified timeframe.

24. The method of claim 22, wherein comparing the first time-series data with the second time-series data comprises calculating a co-variance between the first time-series data and the second time-series data within a specified timeframe.

25. The method of claim 24, wherein determining whether the stopping condition or the discarding condition has occurred comprises:
- calculating a local average co-variance between the first time-series data and the second time-series data, wherein the local average co-variance is calculated with an exponentially weighted moving average filter;
- calculating a ratio of the local average co-variance to the co-variance between the first time-series data and the second time-series data within the specified timeframe; and
- determining whether the calculated ratio changes by a magnitude that is greater than a threshold magnitude.

26. The method of claim 22, further comprising:
- calculating a ratio of an average pulsatile amplitude associated with the first set of time series data to an average non-pulsatile value of the first set of time series data within a specified timeframe; and
- determining whether the stopping condition or the discarding condition occurs by comparing the calculated ratio with a range of expected ratio.

27. The method of claim 22, further comprising:
- calculating a mutual information ("MI") value between the first time-series data and a delayed image of the first time-series data within a specified timeframe, wherein the delayed image is generated by adding a delay to each data point of the first time-series data; and
- determining whether the stopping condition or the discarding condition has occurred by comparing the calculated MI value with a threshold MI value.

* * * * *